United States Patent
Nakamura et al.

(10) Patent No.: US 12,010,954 B2
(45) Date of Patent: Jun. 18, 2024

(54) ADDITIVE FOR MUSHROOM GROWTH MEDIUM

(71) Applicant: SETOLAS HOLDINGS, INC., Takamatsu (JP)

(72) Inventors: Hajime Nakamura, Sakaide (JP); Hikaru Ando, Sakaide (JP)

(73) Assignee: SETOLAS HOLDINGS, INC., Takamatsu (JP)

( * ) Notice: Subject to any disclaimer, the term of this patent is extended or adjusted under 35 U.S.C. 154(b) by 0 days.

(21) Appl. No.: 17/633,457

(22) PCT Filed: Jul. 13, 2020

(86) PCT No.: PCT/JP2020/027220
§ 371 (c)(1),
(2) Date: Feb. 7, 2022

(87) PCT Pub. No.: WO2021/033458
PCT Pub. Date: Feb. 25, 2021

(65) Prior Publication Data
US 2022/0279735 A1    Sep. 8, 2022

(30) Foreign Application Priority Data
Aug. 21, 2019  (JP) .................. 2019-150821

(51) Int. Cl.
*A01G 18/20* (2018.01)
*C12N 1/14* (2006.01)
(52) U.S. Cl.
CPC ............. *A01G 18/20* (2018.02); *C12N 1/14* (2013.01)
(58) Field of Classification Search
CPC ......... A01G 18/00; A01G 18/10; A01G 18/20
USPC ............................................................ 47/1.1
See application file for complete search history.

(56) References Cited

U.S. PATENT DOCUMENTS

| | | | |
|---|---|---|---|
| 4,537,613 A * | 8/1985 | Pebeyre | A01G 18/10 47/1.1 |
| 4,646,466 A * | 3/1987 | Olah | A01G 18/50 47/1.1 |
| 5,018,301 A * | 5/1991 | Kusakabe | A01G 18/20 47/1.1 |

FOREIGN PATENT DOCUMENTS

| | | | |
|---|---|---|---|
| AU | 2018282388 A1 | | 1/2019 |
| CN | 105237111 | * | 1/2016 |
| JP | 4-7649 B2 | | 2/1992 |
| JP | 8-113506 | * | 5/1996 |

(Continued)

OTHER PUBLICATIONS

International Search Report dated Sep. 24, 2020, issued in counterpart International Application No. PCT/JP2020/027220. (2 pages).

(Continued)

*Primary Examiner* — David J Parsley
(74) *Attorney, Agent, or Firm* — WHDA, LLP

(57) ABSTRACT

Provided is an activator for a growth medium used for artificial cultivation of mushrooms, and the activator is used in a growth medium for mushroom artificial cultivation and improves and stabilizes the yield. The activator for a mushroom growth medium includes, as antacid inorganic substances, aluminum, calcium, and magnesium. By changing the proportion of each element, the neutralization function is adjusted. By adding a small amount of the activator, an optimum cultivation pH for an intended type of mushroom is achieved, and the optimum cultivation pH can be maintained.

6 Claims, 5 Drawing Sheets

(56) References Cited

FOREIGN PATENT DOCUMENTS

| | | | |
|---|---|---|---|
| JP | 2673796 | B2 | 11/1997 |
| JP | 11-299347 | A | 11/1999 |
| JP | 2000-102322 | * | 4/2000 |
| JP | 2006-149257 | A | 6/2006 |
| JP | 2006-271303 | * | 10/2006 |
| JP | 4127806 | B2 | 7/2008 |
| JP | 5916026 | B2 | 5/2016 |
| JP | 2019-122352 | A | 7/2019 |
| KR | 2004-0047521 | * | 6/2004 |
| KR | 20190022720 | A | 3/2019 |
| WO | WO 2014/170911 | * | 10/2014 |

OTHER PUBLICATIONS

Extended (Supplementary) European Search Report dated Jul. 14, 2023, issued in counterpart EP application No. 20855260.4. (2 pages).

* cited by examiner

[Fig. 1]
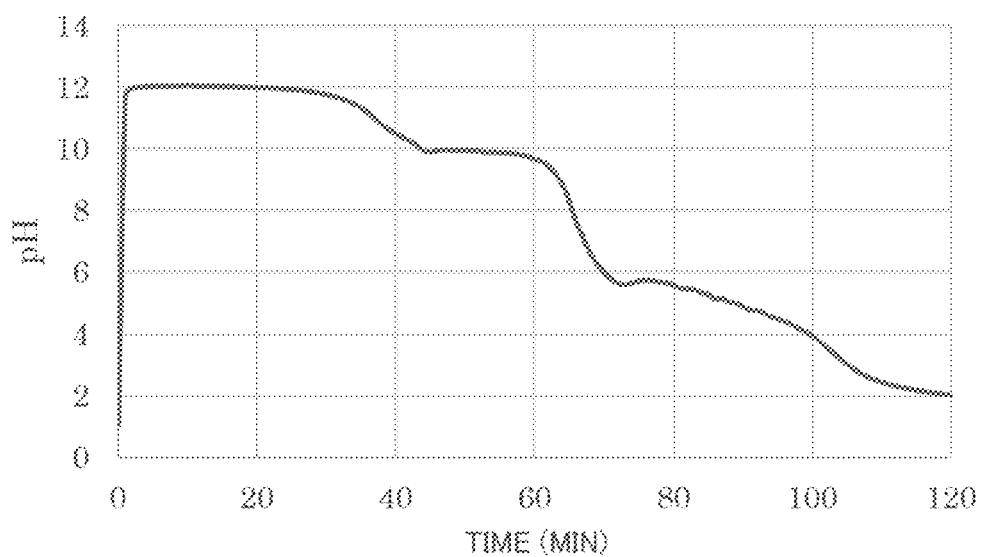
[Fig. 2]
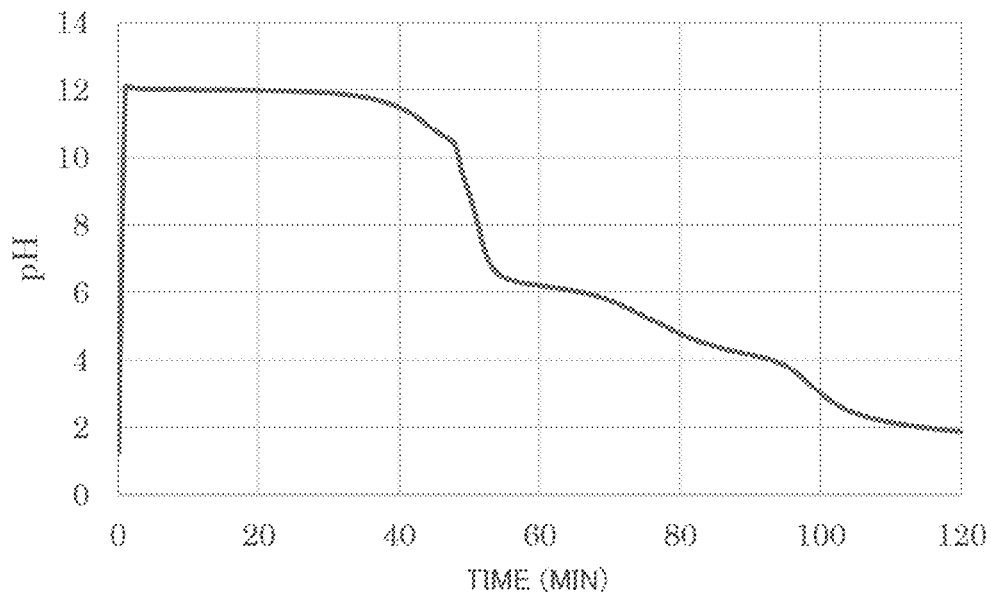

[Fig. 3]
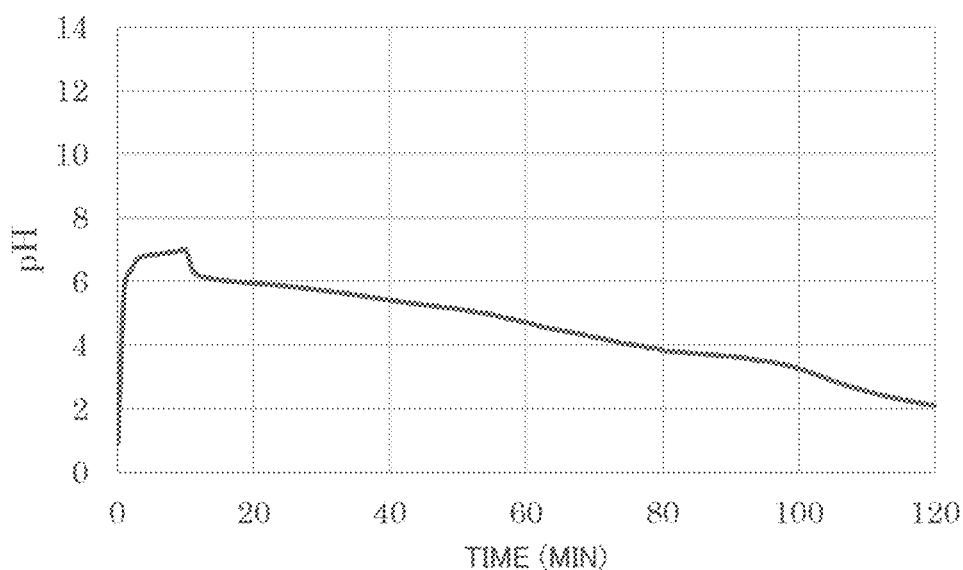
[Fig. 4]
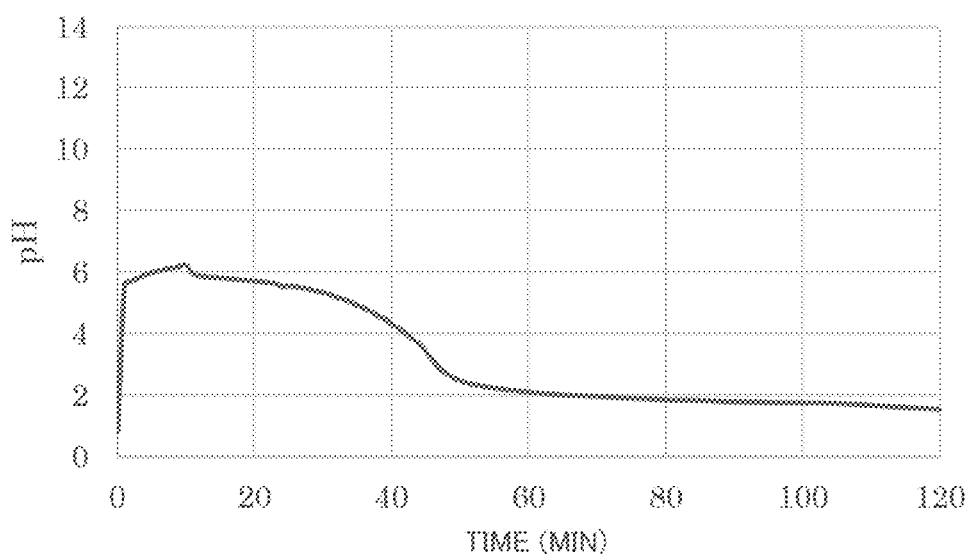

[Fig. 5]
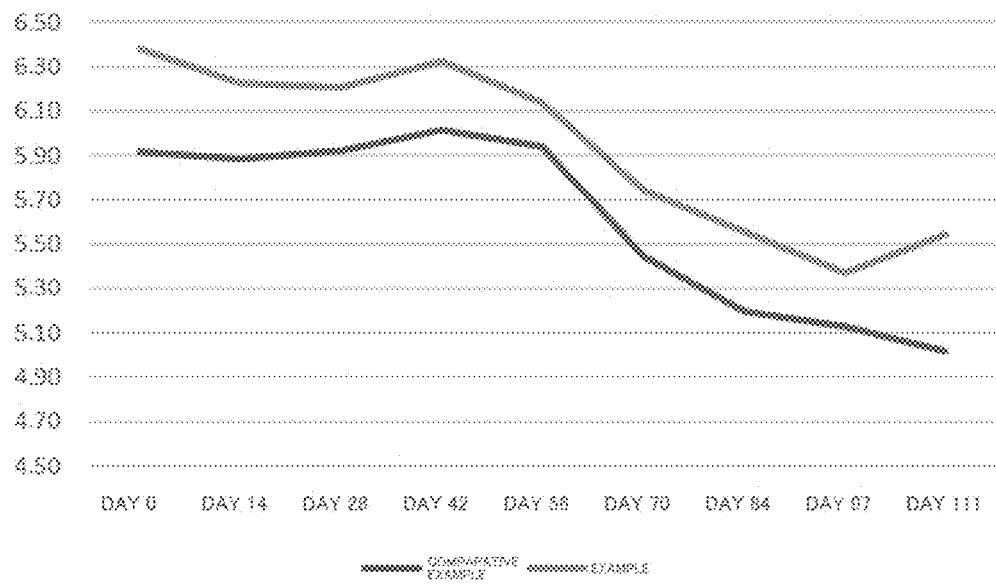
[Fig. 6]
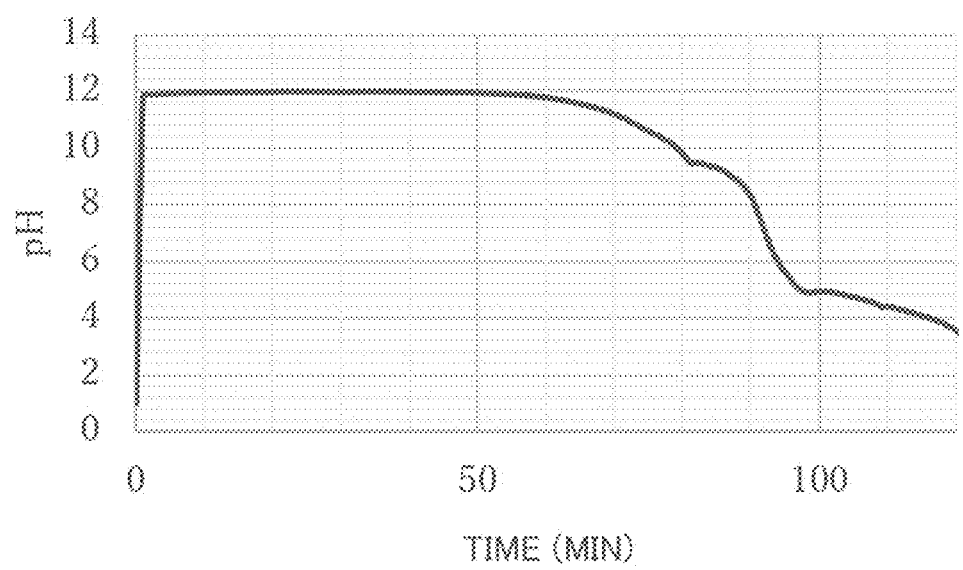

[Fig. 7]
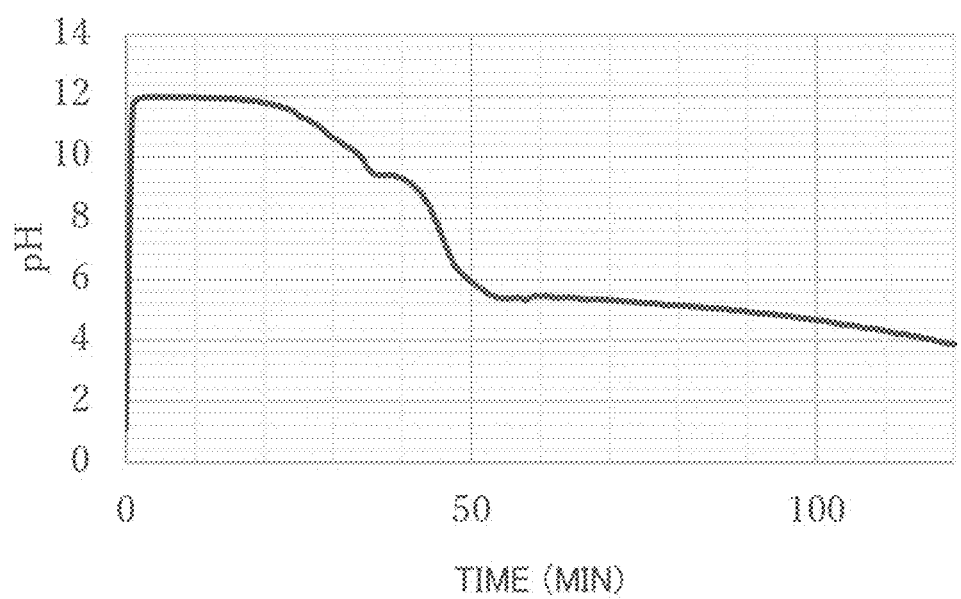
[Fig. 8]
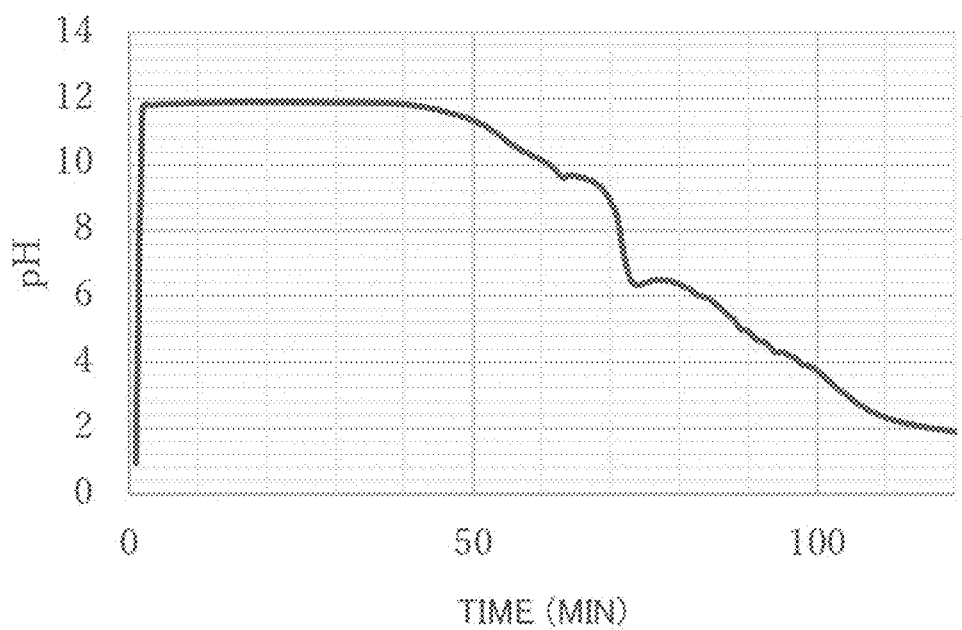

[Fig. 9]
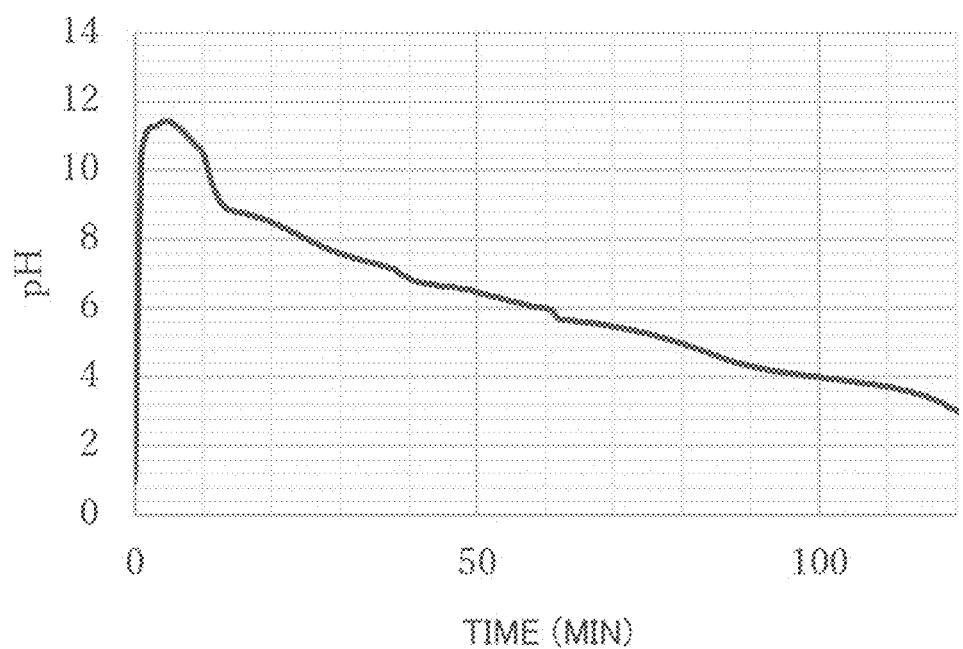

ADDITIVE FOR MUSHROOM GROWTH MEDIUM

TECHNICAL FIELD

The present invention relates to an additive for a growth medium used for artificial cultivation of mushrooms, and the additive can improve and stabilize the yield of any mushroom.

BACKGROUND ART

For mushroom bed cultivation of the artificial cultivation of mushrooms, a growth medium is typically prepared by adding nutrient sources such as rice bran, okara (bean curd refuse), and wheat bran to a base material including sawdust, corn cob meal, bagasse, and beet waste. However, depending on a combination of the materials in a base material, a growth medium may have a lower pH than a pH suitable for mushroom growth (an optimum cultivation pH) in some cases. In other cases, sugars contained in a growth medium packed in a bottle or a bag may partially degrade due to spoilage or the like before high-pressure steam sterilization, and the growth medium may have a lower pH. In such conditions, the mushroom yield is reduced.

To maintain an optimum cultivation pH during mushroom cultivation, techniques in which an antacid inorganic substance or the like (an activator for a mushroom growth medium) is added to adjust the pH in a growth medium to an optimum pH for mushroom cultivation have been disclosed (Patent Documents 1 to 5).

However, a natural lime such as oystershell lime or a synthetic inorganic substance widely used as the activator does not necessarily achieve satisfactory result for some mushrooms (such as *Hypsizygus marmoreus* (bunashimeji), *Pleurotus eryngii* (king oyster mushroom), *Pleurotus ostreatus* (oyster mushroom), and *Agaricus bisporus* (button mushroom)) that need a comparatively high pH or for some growth media having a certain formulation. For example, an inorganic substance such as synthetic aluminum hydroxide and synthetic aluminum silicate contains aluminum as a metal cation exerting an antacid-ability and thus neutralizes acid at a low pH of about 4.0, which may be lower than an optimum cultivation pH for some mushrooms, unfortunately.

RELATED ART DOCUMENTS

Patent Document

Patent Document 1: Japanese Examined Patent Application Publication No. 4-7649
Patent Document 2: Japanese Patent No. 2673796
Patent Document 3: Japanese Patent No. 4127806
Patent Document 4: Japanese Patent Application Publication No. 2006-149257
Patent Document 5: Japanese Patent No. 5916026

SUMMARY

Technical Problem

Each mushroom has its own optimum cultivation pH, and an optimum combination of materials is accordingly selected. For example, for *Hypsizygus marmoreus*, *Pleurotus ostreatus*, or the like, it is believed that a mushroom growth medium is preferably maintained at a pH of about 5.5 to 6.5 when mushroom spawn are inoculated.

The present invention is intended to provide an additive for a mushroom growth medium capable of adjusting a growth medium to an optimum cultivation pH for an intended type of mushroom and of maintaining the optimum cultivation pH.

Various materials are used as components in a basic growth medium. For example, corn cob meal contains characteristic components such as sugars, which are not contained in sawdust, and is actually known to be likely to make a growth medium have an acidic pH of less than 5.5. An antacid compound contained in a basic growth medium has an antacid-function (neutralization function) and prevents oxidation of a mushroom growth medium.

The present invention is intended to provide an additive for a mushroom growth medium. The additive has an antacid-function (neutralization function) to increase the initial pH of a growth medium by 0.5 or more when contained in a mushroom growth medium and increases the mushroom yield.

Solution to Problem

The inventors of the present invention have studied various antacid-agents to find that the above problem can be solved by adding an aluminum compound, a calcium compound, and a magnesium compound as materials at certain proportions and have completed the present invention.

The present invention relates to an additive for a mushroom growth medium in the following aspects (1) to (6).

(1) An additive for a mushroom growth medium, the additive including an aluminum compound, a calcium compound, and a magnesium compound. In the additive for a mushroom growth medium, a proportion of the aluminum compound, a proportion of the calcium compound, and a proportion of the magnesium compound in terms of oxides of $Al_2O_3$, CaO, and MgO are such that a proportion of CaO is more than a proportion of $Al_2O_3$ and a proportion of MgO.

(2) The additive for a mushroom growth medium according to the aspect (1), in which the proportions of the aluminum compound, the calcium compound, and the magnesium compound in terms of the oxides are such that the proportion of $Al_2O_3$ is 3 to 30 wt %, the proportion of CaO is 35 to 60 wt %, and the proportion of MgO is 3 to 30 wt %.

(3) The additive for a mushroom growth medium according to the aspect (1), in which the additive is capable of maintaining a pH of 4.0 or more for 60 minutes or more as antacid-characteristics by modified Fuchs method.

(4) The additive for a mushroom growth medium according to the aspect (1), in which a material of the $Al_2O_3$ is aluminum hydroxide, a material of the CaO is at least one selected from the group consisting of calcium hydroxide, calcium carbonate, calcium oxide, calcium monohydrogen phosphate, calcium monohydrogen phosphate dihydrate, calcium dihydrogen phosphate, dihydrogen phosphate monohydrate, tricalcium phosphate, octacalcium phosphate, calcium sulfate, calcium sulfate hemihydrate, calcium sulfate dihydrate, calcium nitrate, and calcium nitrate tetrahydrate, and a material of the MgO is at least one selected from the group consisting of magnesium hydroxide, magnesium carbonate, magnesium oxide, magnesium monohydrogen phosphate trihydrate, magnesium dihydrogen phosphate tetrahydrate, trimagnesium phosphate octahydrate, magnesium sulfate, magnesium sulfate heptahydrate, magnesium nitrate, magnesium nitrate dihydrate, and magnesium nitrate hexahydrate.
(5) The additive for a mushroom growth medium according to any one of the aspects (1) to (4), in which the additive has a neutralization function to increase a pH of a mushroom growth medium by 0.5 or more at an initial stage when the additive is contained in the growth medium.
(6) The additive for a mushroom growth medium according to any one of the aspects (1) to (4), in which the additive has a neutralization function to increase a pH of a mushroom growth medium by 0.2 or more during cultivation when the additive is contained in the growth medium.

The present invention also relates to a mushroom growth medium in the following aspects (7) and (8).
(7) A mushroom growth medium including the additive for a mushroom growth medium according to any one of the aspects (1) to (4) at a content of 0.01 to 3.0% by weight relative to a weight of the mushroom growth medium after moisture control.
(8) A mushroom growth medium having a function to increase a mushroom yield by 8% or more, the mushroom growth medium including the additive for a mushroom growth medium according to any one of the aspects (1) to (4).

Advantageous Effects of Invention

By adding an additive for a mushroom growth medium of the present invention to a growth medium, the yield of any mushroom can be increased and stabilized as compared with conventional additives for a mushroom growth medium.

BRIEF DESCRIPTION OF DRAWINGS

FIG. 1 is a graph showing antacid-characteristics of an additive for a mushroom growth medium in Example 1.
FIG. 2 is a graph showing antacid-characteristics of an additive for a mushroom growth medium in Example 2.
FIG. 3 is a graph showing antacid-characteristics of an additive for a mushroom growth medium in Example 3.
FIG. 4 is a graph showing antacid-characteristics of an additive for a mushroom growth medium in Comparative Example 1.
FIG. 5 is a graph showing changes in pH of a mushroom growth medium in Example 7 over time.
FIG. 6 is a graph showing antacid-characteristics of an additive for a mushroom growth medium in Test Example 1.
FIG. 7 is a graph showing antacid-characteristics of an additive for a mushroom growth medium in Test Example 2.
FIG. 8 is a graph showing antacid-characteristics of an additive for a mushroom growth medium in Test Example 3.
FIG. 9 is a graph showing antacid-characteristics of an additive for a mushroom growth medium in Test Example 4.

DESCRIPTION OF EMBODIMENTS

Mushroom bed cultivation of the artificial cultivation of mushrooms is performed by using an artificial culture medium containing a base material such as sawdust and corn cob meal and nutrient sources such as rice bran and wheat bran. At the present time, *Lentinus edodes* (shiitake mushroom), *Hypsizygus marmoreus*, *Pleurotus ostreatus*, *Polyporus frondosa* (hen of the woods), *Pleurotus eryngii*, *Pholidota nameko* (nameko), and other mushrooms are produced in an air-conditioned room by the above method. It takes about 5 to 20 weeks from spawn inoculation to harvest, and the mushroom beds after harvest are not recycled but discarded. Cultivation is performed in a room, and thus an environment insusceptible to external environment such as insect pests and destructive fungi is easily prepared. Hence, year-round harvest can be achieved with a stable yield and quality.

The present invention relates to an additive for a growth medium, and the additive is to be added to a growth medium used for the mushroom bed cultivation and has an antacid-function. The additive contains an aluminum compound, a calcium compound, and a magnesium compound, and the proportion of the aluminum compound, the proportion of the calcium compound, and the proportion of the magnesium compound in terms of oxides of $Al_2O_3$, CaO, and MgO are such that the proportion of CaO is more than the proportion of $Al_2O_3$ and the proportion of MgO.

The additive for a mushroom growth medium contains, in terms of oxides, $Al_2O_3$ at 3 to 30 wt %, CaO at 35 to 60 wt %, and MgO at 3 to 30 wt %, for example, and preferably contains, in terms of oxides, $Al_2O_3$ at 3 to 20 wt %, CaO at 35 to 60 wt %, and MgO at 5 to 30 wt %. When containing each element at such a proportion, the additive can exert its antacid-function to maintain an optimum cultivation pH for each mushroom.

For the aluminum compound, the calcium compound, and the magnesium compound contained in the additive of the present invention, the material of aluminum is aluminum hydroxide, the material of calcium is at least one selected from the group consisting of calcium hydroxide, calcium carbonate, calcium oxide, calcium monohydrogen phosphate, calcium monohydrogen phosphate dihydrate, calcium dihydrogen phosphate, dihydrogen phosphate monohydrate, tricalcium phosphate, octacalcium phosphate, calcium sulfate, calcium sulfate hemihydrate, calcium sulfate dihydrate, calcium nitrate, and calcium nitrate tetrahydrate, and the material of magnesium is at least one selected from the group consisting of magnesium hydroxide, magnesium carbonate, magnesium oxide, magnesium monohydrogen phosphate trihydrate, magnesium dihydrogen phosphate tetrahydrate, trimagnesium phosphate octahydrate, magnesium sulfate, magnesium sulfate heptahydrate, magnesium nitrate, magnesium nitrate dihydrate, and magnesium nitrate hexahydrate.

The materials of the additive of the present invention are preferably a compound having a high antacid-function. The material of calcium is more preferably calcium hydroxide, calcium carbonate, or calcium oxide, and the material of magnesium is more preferably magnesium hydroxide, magnesium carbonate, or magnesium oxide. No aluminum compound has a high antacid-function, but an aluminum compound is needed as an adsorbent.

The additive for a mushroom growth medium of the present invention functions to adjust a growth medium to an optimum cultivation pH for an intended type of mushroom and to maintain the optimum cultivation pH by changing materials and the proportion of each element.

The modified Fuchs method for indicating an antacid-function in the present invention is an experiment in which the pH behavior of an additive for a mushroom growth medium is determined in the following procedure.
 1. A pH meter and a constant temperature bath (set at 37±2° C.) are turned on.
 2. The pH meter is calibrated by using pH standard solutions (4.0, 7.0, 9.0).

3. In a 300-mL beaker, exactly measured 50 mL of 0.1 mol/L hydrochloric acid (f=0.990 to 1.010) is placed, and the beaker is set in the constant temperature bath set at a water temperature of 37° C.
4. The tip of a discharge hose of a metering pump adjusted at a dropping amount of 2.0±0.1 mL/min is set in the 300-mL beaker, and a magnetic stirrer is placed and stirred at 300 rpm.
5. After the liquid temperature reaches 37±0.5° C., exactly measured 1.00 g of a sample is added, and simultaneously a stopwatch and a recorder are started.
6. The pH value is recorded 10 minutes after addition of the sample, and the metering pump is immediately operated.
7. A 0.1 mol/L hydrochloric acid is added dropwise at a dropping amount of 2.0±0.1 mL/min for 110 minutes, and the pH behavior is recorded for 120 minutes in total.

In mushroom bed cultivation, after growth for 3 to 4 months, a culture medium is stimulated by fungus scraping to allow fruit bodies to sprout, and the fruit bodies are grown and harvested. The additive for a mushroom growth medium of the present invention has such antacid-characteristics as to maintain a pH of 4.0 or more for 60 minutes or more as determined by modified Fuchs method and can prevent a pH reduction of a mushroom growth medium after mushroom spawn inoculation when contained in the growth medium at 0.01 to 3.0 wt %, preferably 0.1 to 1.0 wt %. Hence, the mushroom yield can be markedly increased by 8% or more.

The present invention will next be described in detail on the basis of examples, but the present invention is not limited to these examples.

In the examples, *Hypsizygus marmoreus* was used to perform growth and cultivation experiments.

Most generally used materials as the growth base material for *Hypsizygus marmoreus* cultivation include two materials of corn cob meal and cedar sawdust. In Examples 1 to 3 and Comparative Examples 1 and 2, a growth medium containing corn cob meal as the base material was used, whereas in Examples 4 to 6 and Comparative Example 3, a growth medium containing cedar sawdust as the base material was used. In each Examples and Comparative Examples, the amount of an additive for a mushroom growth medium was 0.25% by weight relative to the total amount of a growth medium.

Example 1

Growth Medium

First, 124 g of corn cob meal, 40 g of okara, 30 g of wheat bran, and 16 g of rice bran were mixed in terms of dry weight, and water was added so as to give a water content of 65%, giving a growth medium.

Additive for Mushroom Growth Medium

Next, synthetic aluminum hydroxide at a content of 18.3% by weight (10.0% by weight in terms of oxide), calcium hydroxide at a content of 64.5% by weight (48.9% by weight in terms of oxide), and magnesium hydroxide at a content of 17.2% by weight (11.9% by weight in terms of oxide) were mixed to give an additive for a mushroom growth medium of the present invention.

Antacid-Characteristics of Additive for Mushroom Growth Medium: Modified Fuchs Method Antacid-characteristics of the prepared additive for a mushroom growth medium were determined by the modified Fuchs method.

The antacid-characteristics of the additive for a mushroom growth medium used in Example 1 and determined by the modified Fuchs method are shown in FIG. 1.

Mushroom Spawn Growth Step

The prepared additive for a mushroom growth medium was added at 0.25% by weight relative to the total amount of the above growth medium, and the whole was thoroughly mixed. About 600 g of the mixture was packed in each 850-mL polypropylene bottle for mushroom growth (Chikumakasei, 850-58). Six cultivation bottles were prepared and subjected to high pressure steam sterilization at 121° C. for 90 minutes and then were allowed to cool to normal temperature in a clean bench, and *Hypsizygus marmoreus* spawn (Chikumakasei, Chikumush H-120) were inoculated. The cultivation bottles after inoculation were placed in an environment at a temperature of 22° C. and a humidity of 70% RH, and the spawn were grown for 90 days.

Measurement of pH of Growth Medium

In the growth step, 40 g of the growth medium after high pressure steam sterilization but before inoculation of *Hypsizygus marmoreus* spawn was sampled, and 80 mL of ion-exchanged water was added. The whole was shaken at a shaking rate of 160 r/min for a shaking time of 1 hour, and then the pH was determined at 25° C.

Manju Scraping

The lid of the cultivation bottle after completion of the growth step was removed, and fungus scraping was performed around the top center portion about 3.5 cm in diameter on the growth medium to a depth of about 1 cm.

Sprouting Step

After manju scraping, the bottle was filled with water, and the content was submerged in water for 3 hours. Excess water was then discarded. Subsequently, the surface of the cultivation bottle was covered with a transparent porous polyethylene sheet having a thickness of 0.03 mm (manufactured by Okura Industrial, trade name: Yuko-nopori (for rice nursery and special cultivation)), and cultivation was performed for 14 days in an environment at an illumination intensity of 50 Lux, a temperature of 14° C., a humidity of 95% RH, and a $CO_2$ concentration of 2,500 ppm or less.

Growing Step

After completion of the sprouting step, the porous polyethylene sheet on the cultivation bottle was removed, and cultivation was performed for 8 days in an environment at an illumination intensity of 300 Lux, a temperature of 14° C., a humidity of 90% RH, and a $CO_2$ concentration of 2,500 ppm or less. Fruit bodies were then harvested from the cultivation bottle and were immediately weighed.

Example 2

The same experiment as in Example 1 was performed except that an additive for a mushroom growth medium was prepared by mixing synthetic aluminum hydroxide at a content of 18.3% by weight (10.0% by weight in terms of oxide), calcium hydroxide at a content of 64.5% by weight (48.9% by weight in terms of oxide), and magnesium carbonate at a content of 17.2% by weight (8.2% by weight in terms of oxide).

Antacid-characteristics of the additive for a mushroom growth medium used in Example 2 and determined by the modified Fuchs method are shown in FIG. 2.

Example 3

The same experiment as in Example 1 was performed except that an additive for a mushroom growth medium was prepared by mixing synthetic aluminum hydroxide at a content of 18.3% by weight (10.0% by weight in terms of oxide), calcium carbonate at a content of 64.5% by weight (36.2% by weight in terms of oxide), and magnesium hydroxide at a content of 17.2% by weight (11.9% by weight in terms of oxide).

Antacid-characteristics of the additive for a mushroom growth medium used in Example 3 and determined by the modified Fuchs method are shown in FIG. 3.

Comparative Example 1

The same experiment as in Example 1 was performed except that calcium carbonate (manufactured by Nittetsu Mining) was used as the additive for a mushroom growth medium. Antacid-characteristics of the additive for a mushroom growth medium used in Comparative Example 1 and determined by the modified Fuchs method are shown in FIG. 4.

Comparative Example 2

The same experiment as in Example 1 was performed except that no additive for a mushroom growth medium was added.

The experimental results of Examples 1 to 3 and Comparative Examples 1 and 2 are shown in Table 1. Increased yields of fruit bodies are calculated on the basis of Comparative Example 2.

In Examples 4 to 6 and Comparative Example 3 described below, a growth medium containing cedar sawdust as the base material was used. The amount of an activator for a mushroom growth medium was 0.25 wt % relative to the total amount of a growth medium.

Example 4

The same experiment as in Example 1 was performed except that a growth medium was prepared by mixing 80 g of cedar sawdust, 60 g of rice bran, 30 g of corn cob meal, 20 g of okara, and 20 g of wheat bran in terms of dry weight and then adding water so as to give a water content of 65%.

Example 5

The same experiment as in Example 4 was performed except that an additive for a mushroom growth medium was prepared in the same manner as in Example 2 by mixing synthetic aluminum hydroxide at a content of 18.3% by weight (10.0% by weight in terms of oxide), calcium hydroxide at a content of 64.5% by weight (48.9% by weight in terms of oxide), and magnesium carbonate at a content of 17.2% by weight (8.2% by weight in terms of oxide).

Example 6

The same experiment as in Example 4 was performed except that an additive for a mushroom growth medium was prepared in the same manner as in Example 3 by mixing synthetic aluminum hydroxide at a content of 18.3% by weight (10.0% by weight in terms of oxide), calcium carbonate at a content of 64.5% by weight (36.2% by weight in terms of oxide), and magnesium hydroxide at a content of 17.2% by weight (11.9% by weight in terms of oxide).

TABLE 1

| | | Example 1 | Example 2 | Example 3 | Comp. Example 1 | Comp. Example 2 |
|---|---|---|---|---|---|---|
| pH of growth medium (25° C.) | | 6.2 | 6.2 | 6.1 | 5.9 | 5.5 |
| Average yield (g/bottle) | | 210.3 ± 6.4 | 200.7 ± 13.7 | 198.8 ± 12.6 | 192.3 ± 16.1 | 184.4 ± 9.9 |
| Increased yield (%) | | 14 | 9 | 8 | 4 | — |
| Amount of activator (wt %/total amount of growth medium) | | 0.25 | 0.25 | 0.25 | 0.25 | Without addition |
| Material | Aluminum hydroxide (wt %) | 18.3 | 18.3 | 18.3 | — | — |
| | (value in terms of oxide wt %) | (10.0) | (10.0) | (10.0) | | |
| | Calcium hydroxide (wt %) | 64.5 | 64.5 | — | — | — |
| | (value in terms of oxide (wt %)) | (48.9) | (48.9) | | | |
| | Calcium carbonate (wt %) | — | — | 64.5 | 100 | — |
| | (value in terms of oxide (wt %)) | | | (36.2) | (56.2) | |
| | Magnesium hydroxide (wt %) | 17.2 | — | 17.2 | — | — |
| | (value in terms of oxide (wt %)) | (11.9) | | (11.9) | | |
| | Magnesium carbonate (wt %) | — | 17.2 | — | — | — |
| | (value in terms of oxide (wt %)) | | (8.2) | | | |

As shown in Table 1, the fruit body yield markedly improved when cultivation was performed by using a growth medium containing the additive of the present invention. In particular, the growth medium containing the additive containing aluminum hydroxide, calcium hydroxide, and magnesium hydroxide as materials (Example 1) achieved the highest yield.

Comparative Example 3

The same experiment as in Example 4 was performed except that no additive for a mushroom growth medium was added.

The experimental results in Examples 4 to 6 and Comparative Example 3 are shown in Table 2.

TABLE 2

|  | Example 4 | Example 5 | Example 6 | Comp. Example 3 |
|---|---|---|---|---|
| pH of growth medium (25° C.) | 6.5 | 6.5 | 6.4 | 5.9 |
| Average yield (g/bottle) | 138.9 ± 7.6 | 137.0 ± 6.7 | 132.6 ± 6.3 | 122.2 ± 8.3 |
| Increased yield (%) | 14 | 12 | 8 | — |
| Amount of activator (wt %/total amount of growth medium) | 0.25 | 0.25 | 0.25 | Without addition |
| Material Aluminum hydroxide (wt %) | 18.3 | 18.3 | 18.3 | — |
| (value in terms of oxide (wt %)) | (10.0) | (10.0) | (10.0) |  |
| Calcium hydroxide (wt %) | 64.5 | 64.5 | — | — |
| (value in terms of oxide (wt %)) | (48.9) | (48.9) |  |  |
| Calcium carbonate (wt %) | — | — | 64.5 | — |
| (value in terms of oxide (wt %)) |  |  | (36.2) |  |
| Magnesium hydroxide (wt %) | 17.2 | — | 17.2 | — |
| (value in terms of oxide (wt %)) | (11.9) |  | (11.9) |  |
| Magnesium carbonate (wt %) | — | 17.2 | — | — |
| (value in terms of oxide (wt %)) |  | (8.2) |  |  |

As shown in Table 2, the fruit body yield markedly improved when cultivation was performed by using a growth medium containing the additive of the present invention. In particular, the growth medium containing the activator containing aluminum hydroxide, calcium hydroxide, and magnesium hydroxide as materials (Example 4) achieved the highest yield.

Example 7

Changes in pH of a growth medium containing the additive of the present invention were determined over time.

Substantially the same experiment as in Example 6 was performed. The additive for a mushroom growth medium used in Example 6 was added at 0.25% by weight relative to the total amount of the same growth medium as in Example 4. After inoculation of *Hypsizygus marmoreus* spawn, 40 g of the growth medium was sampled every two weeks during cultivation, and 80 mL of ion-exchanged water was added. The whole was shaken at a shaking rate of 160 r/min for a shaking time of 1 hour, and then the pH was determined at 25° C.

As a control, a growth medium without the additive of the present invention was used. The results are shown in Table 3 and FIG. 5.

TABLE 3

|  | Day 0 | Day 14 | Day 28 | Day 42 | Day 56 | Day 70 | Day 84 | Day 97 | Day 111 |
|---|---|---|---|---|---|---|---|---|---|
| Control | 5.91 | 5.89 | 5.92 | 6.02 | 5.94 | 5.44 | 5.20 | 5.13 | 5.02 |
| Example | 6.41 | 6.23 | 6.21 | 6.33 | 6.14 | 5.74 | 5.56 | 5.37 | 5.55 |

As shown in Table 3, when mushrooms were cultivated on a growth medium containing the additive of the present invention, it was ascertained that the pH of the growth medium during cultivation was at least 0.2 higher than that of the control. Addition of the additive of the present invention should adjust the pH of a growth medium to an optimum mushroom cultivation pH.

Example 8

The proportions of the aluminum compound, the calcium compound, and the magnesium compound contained in an additive for a mushroom growth medium were changed as shown in Test Examples 1 to 4, and antacid-functions were evaluated by the modified Fuchs method. Each numerical value in parentheses is a weight in terms of oxide. Each unit % is % by weight.

Test Example 1: aluminum hydroxide at a content of 10% (5%)
  calcium hydroxide at a content of 79% (60%)
  magnesium hydroxide at a content of 11% (8%)
Test Example 2: aluminum hydroxide at a content of 10% (5%)
  calcium hydroxide at a content of 46% (35%)
  magnesium hydroxide at a content of 44% (30%)
Test Example 3: aluminum hydroxide at a content of 10% (5%)
  calcium oxide at a content of 50% and calcium nitrate tetrahydrate at a content of 30% (57%)
  magnesium oxide at a content of 10% (26%)
Test Example 4: aluminum hydroxide at a content of 10% (5%)
  calcium oxide at a content of 35% (35%)
  magnesium carbonate at a content of 55% (26%)

The results of the modified Fuchs method in Test Examples 1 to 4 are shown in FIGS. 6 to 9, respectively. Each additive of the present invention in Test Examples 1 to 4 exerted a sufficient antacid-function to maintain a mushroom growth medium at a pH of 4.0 or more for 60 minutes or more as antacid-characteristics determined by the modified Fuchs method.

Next, the additive for a mushroom growth medium in Example 1 was used to perform cultivation experiments while the amount of the additive was changed relative to the total amount the growth medium.

Example 9

The same experiment as in Example 1 was performed except that the following materials in different lots from those used in Example 1 were used. The amount of the additive for a mushroom growth medium was 0.25% by weight relative to the total amount of the growth medium.

Growth medium: corn cob meal, okara, wheat bran, and rice bran

*Hypsizygus marmoreus* spawn: Chikumakasei, Chikumush H-120

Example 10

The same experiment as in Example 9 was performed except that the amount of an additive for a mushroom growth medium was 0.025% by weight relative to the total amount of the growth medium.

Example 11

The same experiment as in Example 9 was performed except that the amount of an additive for a mushroom growth medium was 0.125% by weight relative to the total amount of the growth medium.

Comparative Example 4

The same experiment as in Example 9 was performed except that no additive for a mushroom growth medium was added.

The experimental results of Examples 9 to 11 and Comparative Example 4 are shown in Table 4. Increased yields of fruit bodies are calculated on the basis of Comparative Example 4.

TABLE 4

| | Example 9 | Example 10 | Example 11 | Comp. Example 4 |
|---|---|---|---|---|
| pH of growth medium (25° C.) | 6.2 | 5.7 | 5.9 | 5.6 |
| Average yield (g/bottle) | 194.7 ± 8.5 | 193.8 ± 8.4 | 196.8 ± 4.9 | 175.9 ± 6.3 |
| Increased yield (%) | 11 | 10 | 12 | — |
| Amount of activator (wt %/ total amount of growth medium) | 0.25 | 0.025 | 0.125 | Without addition |
| Material Aluminum hydroxide (wt %) | 18.3 | 18.3 | 18.3 | — |
| (value in terms of oxide (wt %)) | (10.0) | (10.0) | (10.0) | |
| Calcium hydroxide (wt %) | 64.5 | 64.5 | 64.5 | — |
| (value in terms of oxide (wt %)) | (48.9) | (48.9) | (48.9) | |
| Magnesium hydroxide (wt %) | 17.2 | 17.2 | 17.2 | — |
| (value in terms of oxide (wt %)) | (11.9) | (11.9) | (11.9) | |

In Example 1 and Example 9, the composition and the amount of the additive for a mushroom growth medium of the present invention are the same, but the average yield was lower in Example 9. This is supposedly because corn cob meal, okara, wheat bran, rice bran, and *Hypsizygus marmoreus* spawn in different lots were used in growth media. In Comparative Example 2 and Comparative Example 4, the average yield was also lower in Comparative Example 4 supposedly due to the same reason.

As apparent from the result of Table 4, the fruit body yield also markedly improved when cultivation was performed by using a growth medium containing the additive for a mushroom growth medium of the present invention.

The invention claimed is:

1. An additive for a mushroom growth medium, the additive comprising:
   an aluminum compound;
   a calcium compound; and
   a magnesium compound, wherein
   a mixing proportion of the aluminum compound, a mixing proportion of the calcium compound, and a mixing proportion of the magnesium compound in terms of oxides of $Al_2O_3$, $CaO$, and $MgO$ are such that the proportion of $CaO$ is more than the proportion of $Al_2O_3$ and the proportion of $MgO$, the proportion of $Al_2O_3$ being 3 to 30 wt %, the proportion of $CaO$ being 35 to 60 wt %, and the proportion of $MgO$ is 3 to 30 wt %,
   wherein the aluminum compound is aluminum hydroxide, and
   wherein the aluminum compound, the calcium compound, and the magnesium compound exist in a state of a mixture thereof without any chemical change such that the additive is capable of maintaining a pH of 4.0 or more for 60 minutes or more as antacid-characteristics by modified Fuchs method.

2. The additive for a mushroom growth medium according to claim 1, wherein a material of the CaO is at least one selected from the group consisting of calcium hydroxide, calcium carbonate, calcium oxide, calcium monohydrogen phosphate, calcium monohydrogen phosphate dihydrate, calcium dihydrogen phosphate, dihydrogen phosphate monohydrate, tricalcium phosphate, octacalcium phosphate, calcium sulfate, calcium sulfate hemihydrate, calcium sulfate dihydrate, calcium nitrate, and calcium nitrate tetrahydrate, and a material of the MgO is at least one selected from the group consisting of magnesium hydroxide, magnesium carbonate, magnesium oxide, magnesium monohydrogen phosphate trihydrate, magnesium dihydrogen phosphate tetrahydrate, trimagnesium phosphate octahydrate, magnesium sulfate, magnesium sulfate heptahydrate, magnesium nitrate, magnesium nitrate dihydrate, and magnesium nitrate hexahydrate.

3. The additive for a mushroom growth medium according to claim 1, wherein the additive has a neutralization function to increase a pH of a mushroom growth medium by 0.5 or more at an initial stage when the additive is contained in the growth medium.

4. The additive for a mushroom growth medium according to claim 1, wherein the additive has a neutralization function to increase a pH of a mushroom growth medium by 0.2 or more during cultivation when the additive is contained in the growth medium.

5. A mushroom growth medium comprising:
   the additive for a mushroom growth medium according to claim 1 at a content of 0.01 to 3.0% by weight relative to a weight of the mushroom growth medium after moisture control.

6. A mushroom growth medium having a function to increase a mushroom yield by 8% or more, the mushroom growth medium comprising:
   the additive for a mushroom growth medium according to claim 1.

* * * * *